(12) United States Patent
Guignet et al.

(10) Patent No.: US 11,946,926 B2
(45) Date of Patent: Apr. 2, 2024

(54) METHOD AND APPARATUS FOR TESTING A BIOLOGICAL SAMPLE

(71) Applicant: BIO-RAD EUROPE GMBH, Basel (CH)

(72) Inventors: Emmanuel Guignet, Cressier (CH); Stephane Bombard, Cressier (CH)

(73) Assignee: Bio-Rad Europe GmbH, Basel (CH)

( * ) Notice: Subject to any disclaimer, the term of this patent is extended or adjusted under 35 U.S.C. 154(b) by 336 days.

(21) Appl. No.: 16/955,014

(22) PCT Filed: Dec. 18, 2018

(86) PCT No.: PCT/EP2018/085468
§ 371 (c)(1),
(2) Date: Jun. 17, 2020

(87) PCT Pub. No.: WO2019/121665
PCT Pub. Date: Jun. 27, 2019

(65) Prior Publication Data
US 2020/0378947 A1    Dec. 3, 2020

(30) Foreign Application Priority Data
Dec. 19, 2017    (EP) .................. 17208591

(51) Int. Cl.
*G01N 33/49* (2006.01)
*B01L 9/06* (2006.01)
(Continued)

(52) U.S. Cl.
CPC .............. *G01N 33/491* (2013.01); *B01L 9/06* (2013.01); *G01N 1/38* (2013.01); *G01N 15/042* (2013.01);
(Continued)

(58) Field of Classification Search
CPC ....... B01L 2200/025; B01L 2300/0627; B01L 9/06; G01N 1/38; G01N 15/042;
(Continued)

(56) References Cited

U.S. PATENT DOCUMENTS 3,028,075 A  *  4/1962  Blum ................... B04B 5/0421
                                                   494/20
2014/0057770 A1* 2/2014  Holmes .................... B04B 7/08
                                                   494/10

FOREIGN PATENT DOCUMENTS

EP    0791394 A2    8/1997
EP    2124054 A1    11/2009
(Continued)

OTHER PUBLICATIONS

Halvorsen et al."Massively Parallel Single-Molecule Manipulation Using Centrifugal Force", Biophysical Journal, vol. 98, Issue 11, pp. L53-L55, ISSN 0006-3495 (Year: 2010).*
(Continued)

*Primary Examiner* — Lyle Alexander
*Assistant Examiner* — Jonathan Bortoli
(74) *Attorney, Agent, or Firm* — Kilpatrick Townsend & Stockton LLP

(57) ABSTRACT

A method of testing a biological sample, the method comprising: providing a centrifuge sample holder having a camera; arranging a transparent container comprising a fluid test medium in a recess of said centrifuge sample holder, wherein the camera is arranged to image a portion of the container comprising said fluid test medium; arranging said biological sample above and not in contact with said fluid test medium in said container; and with the camera, imaging a mixing of said biological sample with said fluid test medium while centrifuging the sample holder.

16 Claims, 9 Drawing Sheets

(51) Int. Cl.
  *G01N 1/38* (2006.01)
  *G01N 15/04* (2006.01)
  *G01N 15/05* (2006.01)
  *G01N 35/00* (2006.01)

(52) U.S. Cl.
  CPC ....... *G01N 15/05* (2013.01); *G01N 35/00029* (2013.01); *B01L 2200/025* (2013.01); *B01L 2300/0627* (2013.01); *G01N 2015/047* (2013.01); *G01N 2035/00148* (2013.01); *G01N 2035/00495* (2013.01)

(58) Field of Classification Search
  CPC ............. G01N 15/05; G01N 2015/047; G01N 2035/00148; G01N 2035/00495; G01N 21/07; G01N 33/491; G01N 35/00029
  See application file for complete search history.

(56) References Cited

FOREIGN PATENT DOCUMENTS

| | | | | |
|---|---|---|---|---|
| EP | 2835178 A1 | * | 2/2015 | ............. B01L 13/02 |
| WO | 2008120516 A1 | | 10/2008 | |
| WO | 2009120516 A1 | | 10/2009 | |
| WO | 2016160962 A1 | | 10/2016 | |
| ZA | 9700849 B | | 7/1998 | |

OTHER PUBLICATIONS

Yang et al. "Multiplexed single-molecule force spectroscopy using a centrifuge". Nat Commun 7, 11026 (2016) (Year: 2016).*

Extended European Search Report from EPO Patent Application No. 17208591.2 dated Jul. 4, 2018.

PCT International Preliminary Report on Patentability (Chapter I) with Written Opinion from PCT/EP2018/085468 dated Jun. 23, 2020.

International Search Report in the international application No. PCT/EP2018/085468, dated May 24, 2019.

Written Opinion of the International Searching Authority in the international application No. PCT/EP2018/085468, dated May 24, 2019.

Colin Mcphee et al.: "High Speed Centrifuge" In: "Developments in Petroleum Science 64: Core Analysis: a Best Practice", Jan. 1, 2015 (Jan. 1, 2015), Elsevier, XP055581758, ISBN: 278-0-444-63533-4, pp. 457-460, p. 457-p. 459; figure 9,4.

English translation of Office Action dated Apr. 1, 2022 in CN Patent Application No. 201880081366.2. 12 pages.

* cited by examiner

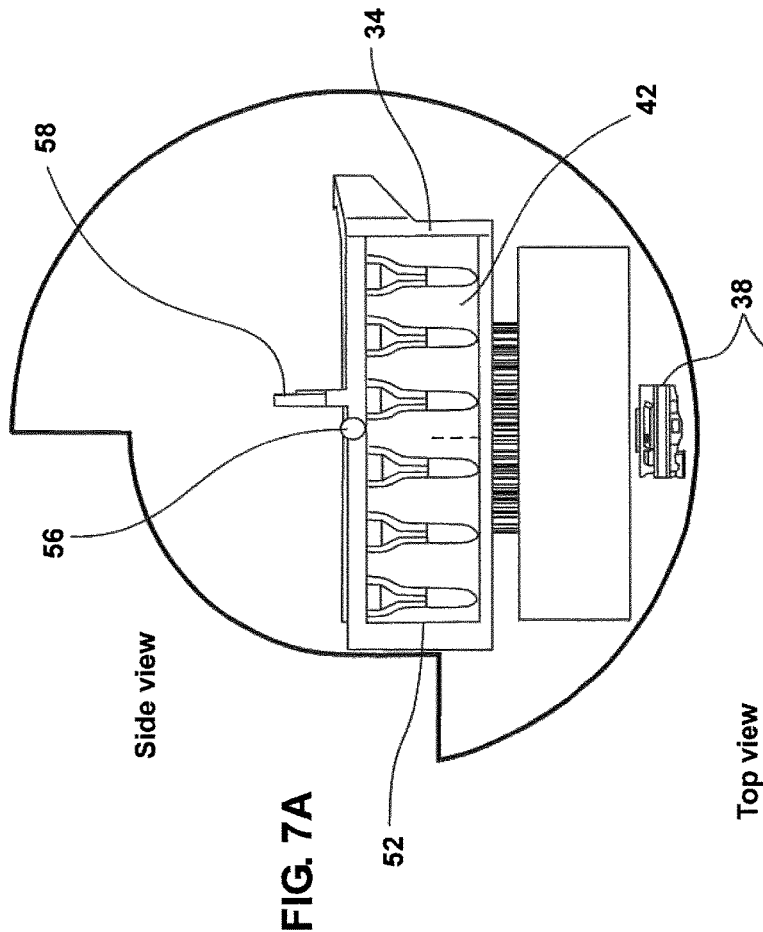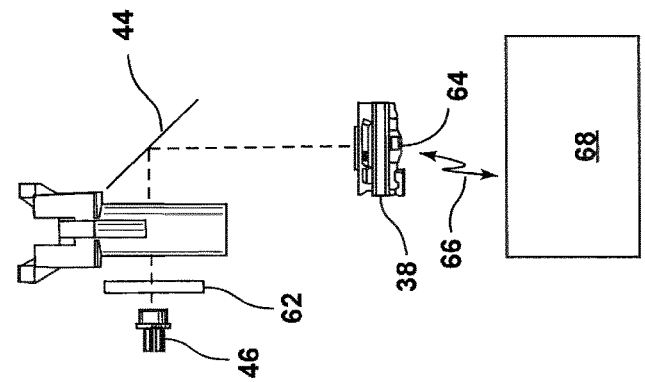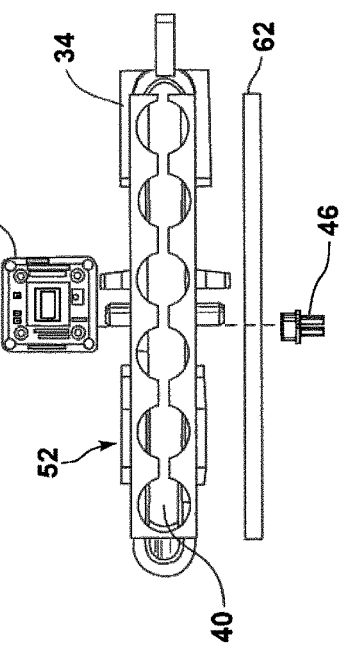

METHOD AND APPARATUS FOR TESTING A BIOLOGICAL SAMPLE

CROSS-REFERENCE TO RELATED APPLICATIONS

This application claims priority to and claims the benefit of PCT Application PCT/EP2018/085468, filed on Dec. 18, 2018, which claims priority to and claims benefit of EP Application No. 17208591.2 filed Dec. 19, 2017, the disclosures of which are incorporated herein by reference.

TECHNICAL FIELD

This presentation relates to a method and corresponding apparatus for testing a biological sample using a centrifuge, in particular a biological sample introduced in a gel-card.

BACKGROUND

A centrifuge is an apparatus that puts an object in rotation around a fixed axis, applying a strong outward force perpendicular to the axis of spin. A centrifuge works using the sedimentation principle, where the centripetal acceleration causes denser substances and particles to move outward in the radial direction. At the same time, objects that are less dense are displaced and move to the center. When centrifuging fluids or materials of different densities in a sample tube, the radial acceleration causes denser fluids or materials to settle to the bottom of the tube, while low-density fluids or materials usually rise to the top.

A plurality of sample tubes can be gathered in a known manner in a "gel card" 10 as illustrated in FIG. 1. The sample tubes can be microtubules 12 and can be filled with a test medium, for example a fluid test medium 14 (eventually comprising reactant 14 for a biological sample to be analyzed). For example, if the biological sample is blood or a blood derivative (e.g., plasma, serum or red blood cells), a fluid test medium in the microtubules can comprise a dextran acrylamide gel, which can contain a reticulation agent, for example a secondary antibody (e.g., anti-human globulin or anti-human IgA antibody). A biological sample comprising patient serum (or plasma) and a reagent, for example, reagent red blood cells or coated particles having an antigen or antibody thereon, can then be added to the microtubules 12 via a top pipette port 16 of the microtubule 12, before incubating the card (e.g. at 37° C. for 15 minutes) and centrifuging the card 10 for a predetermined time (e.g. 10 minutes).

In a centrifuge, the sample containers (such as card 10 above) are generally held in a sample holder or "gondola" or "swinging bucket". The sample holder has a sample container-holding recess that is maintained essentially vertical, with an upward-facing input port, when the centrifuge is at rest. The sample container can thus be "dropped" into the recess through the input port when the centrifuge is at rest. The sample holder is hingedly connected to an outer end of an arm or rotor of the centrifuge, such that the sample container-holding recess and the sample container are maintained essentially horizontal by the acceleration when the centrifuge is in operation, thus accelerating the sample in a radial direction away from the axis of spin. A centrifuge generally comprises a plurality of sample holders attached to a rotating part of the centrifuge, such as centrifuge arms or a centrifuge rotor, thus allowing the centrifuging of a plurality of sample containers at a same time.

An inconvenient of using a known centrifuge is that one needs to wait for the centrifuging operation to end prior to being capable of evaluating the results of the centrifuging.

FIG. 2 illustrates schematically an immunodiagnostic testing apparatus 20 such as described in EP 2,124,054; comprising a centrifuge 22, at least one imager 24 disposed in proximity to said centrifuge such that at least one image can be captured of at least one test element 26 prior to the conclusion of a predetermined centrifuging time period wherein said test element is capable of producing a perceivable agglutination reaction that can be graded, said reaction being accelerated by centrifuging. The captured image of the test element taken prior to the conclusion of the predetermined centrifuging period includes predictive data indicative of whether testing can be stopped in advance of the conclusion of the centrifuging time period, thus allowing a reduction of the centrifuging time. The inventors have noted however that in an apparatus as illustrated in FIG. 2, the imager 24 has only a limited time to capture a picture of each test element 26 while the centrifuge is rotating, said limited time decreasing with the number of test elements 26 carried by the centrifuge 22 (for a given centrifuge speed). Further, the more test elements 26 the centrifuge 22 carries, the longer the field of vision of the imager 24 is obstructed before any particular test element 26 can be imaged by imager 24, and the more the time to capture a picture of each test element 26 is limited. It follows from the above drawbacks that the centrifuge 22 can hardly comprise more than four test elements 26 to operate properly, even with a high-quality camera imager 24, which makes the apparatus expensive to build and operate.

As outlined above, an apparatus as shown in FIG. 2 only allows observing a maximum number of four test elements 26 during centrifuging, and only with an expensive camera 24 capable of acquiring a picture very fast. There exists a need for a method and/or apparatus that would allow imaging more than four test elements while the samples are centrifuged.

Further, no method is known that allows checking automatically that the test elements introduced in the centrifuge are suitable for centrifuging. As detailed hereafter, a test element can be improper for centrifuging; either because it uses a stale or dried up test medium or because the biological sample was improperly put in contact too early with a test medium, for example, before the start of the centrifugation step. There exists a need for a method and/or apparatus that would allow checking automatically that the test elements introduced in the centrifuge are suitable for centrifuging.

SUMMARY

Embodiments of this presentation provides for a method of testing a biological sample that comprises arranging said biological sample in a test container having a fixed relationship with a camera or imaging device, and imaging a displacement of the biological sample in the test container while centrifuging the test container.

An embodiment of this presentation relates to a method of testing a biological sample, the method comprising: providing a centrifuge sample holder having a camera; arranging a transparent container comprising a test medium in a recess of said centrifuge sample holder, wherein the camera is arranged to image a portion of the container comprising said test medium; arranging said biological sample above and not in contact with said test medium in said container; and with the camera, imaging a mixing of said biological sample with said test medium while centrifuging the sample holder.

According to an embodiment of this presentation, the method further comprises imaging with the camera said arranging said biological sample above and not in contact with said test medium in said container.

According to an embodiment of this presentation, the method further comprises imaging with the camera said test medium in said container before said arranging said biological sample above and not in contact with said test medium in said container.

According to an embodiment of this presentation, the method further comprises imaging with the camera the top surface of the test medium while centrifuging the sample holder.

According to an embodiment of this presentation, the method further comprises hingedly coupling said centrifuge sample holder to a rotating part of a centrifuge.

According to an embodiment of this presentation, the centrifuge sample holder having a camera is one of a plurality of centrifuge sample holder having each a camera; and each hingedly coupled to a rotating part of said centrifuge.

According to an embodiment of this presentation, the method further comprises providing a mirror between the camera and the container.

According to an embodiment of this presentation, the method further comprises providing a source of light arranged for illuminating the portion of the container comprising said test medium that is imaged by the camera.

According to an embodiment of this presentation, the source of light is arranged for illuminating by transparency the portion of the container comprising said test medium that is imaged by the camera.

According to an embodiment of this presentation, the recess is arranged for receiving a plurality of transparent containers comprising each a test medium, and the camera is arranged to image at least a portion of each of said plurality of containers received in said recess.

According to an embodiment of this presentation, the camera comprises at least two cameras arranged each to image different containers or different portions of one container.

According to an embodiment of this presentation, the plurality of transparent containers are joined together so as to form a row along an edge of a plastic card.

An embodiment of this presentation also comprises an apparatus for testing a biological sample, the apparatus comprising: a centrifuge sample holder having a camera; the centrifuge sample holder comprising a recess arranged for receiving a transparent container comprising a test medium, wherein the camera is arranged to image a portion of the container comprising said test medium when said container is received in said recess; the camera being arranged for, while the container is centrifuged, imaging a mixing of said test medium with a biological sample arranged prior to centrifuging the container above and not in contact with said test medium in said container.

According to an embodiment of this presentation, the camera is arranged for imaging said biological sample being arranged above and not in contact with said test medium in said container.

According to an embodiment of this presentation, the camera is arranged for imaging said test medium in said container before said biological sample being arranged above and not in contact with said test medium in said container.

According to an embodiment of this presentation, the camera is arranged for also imaging the top surface of the test medium while centrifuging the sample holder.

According to an embodiment of this presentation, the apparatus further comprises a centrifuge for centrifuging said centrifuge sample holder, the centrifuge sample holder being hingedly coupled to a rotating part of said centrifuge.

According to an embodiment of this presentation, said centrifuge sample holder having a camera is one of a plurality of centrifuge sample holder having each a camera and each hingedly coupled to a rotating part of said centrifuge.

According to an embodiment of this presentation, the apparatus further comprises a mirror between the camera and the container.

According to an embodiment of this presentation, the apparatus further comprises a source of light arranged for illuminating the portion of the container comprising said test medium that is imaged by the camera.

According to an embodiment of this presentation, the source of light is arranged for illuminating by transparency the portion of the container comprising said test medium that is imaged by the camera.

According to an embodiment of this presentation, the recess is arranged for receiving a plurality of transparent containers comprising each a test medium, the camera being arranged to image at least a portion of each of said plurality of containers received in said recess.

According to an embodiment of this presentation, the camera comprises at least two cameras arranged each to image different containers. According to an embodiment of this presentation, the plurality of transparent containers are joined together so as to form a row along an edge of a plastic card.

These and other features and advantages will become further apparent from the detailed description and accompanying figures that follow. In the figures and description, numerals indicate the various features; like numerals referring to like features throughout both the drawings and the description.

BRIEF DESCRIPTION OF THE DRAWINGS

FIG. 7A is a side view of portions of a centrifuge sample holder according to embodiments of this presentation.

FIG. 7B is a top view of the portions of the centrifuge sample holder of FIG. 7A.

FIG. 7C is a front view of the portions of the centrifuge sample holder of FIG. 7A.

DETAILED DESCRIPTION

Figure 1:
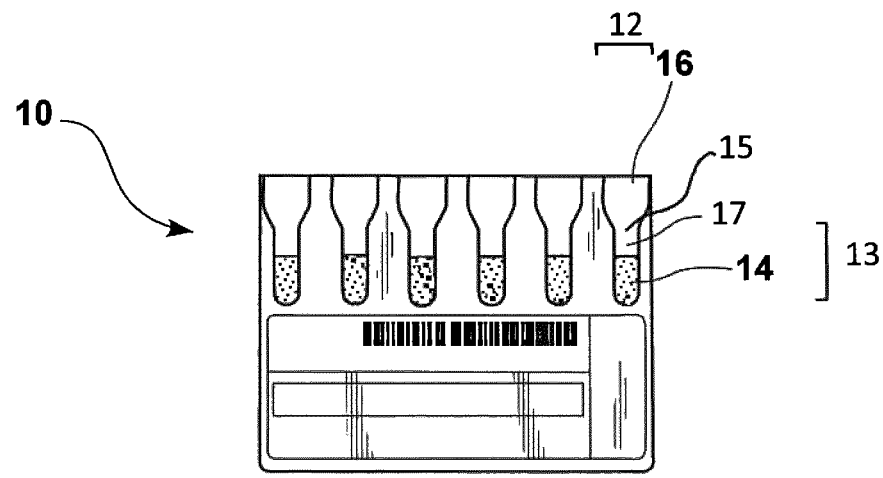
FIG. 1 illustrates a known sample gel card that can be used in embodiments of this presentation.

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

An embodiment of the invention relates to a method of testing a biological sample, the method comprising: providing a centrifuge sample holder having a camera; arranging a transparent container comprising a test medium in a recess of said centrifuge sample holder, wherein the camera is arranged to image a portion of the container comprising said test medium; arranging the biological sample above, and not in contact with, said test medium in said container; and with the camera, imaging a mixing of said biological sample with said test medium while centrifuging the sample holder. In this presentation, a "transparent" container is a container having at least one portion that is transparent enough to the waves used by the sensor/camera to allow the sensor/camera to image the inside of the container. The test medium can be a fluid or a gel or a porous medium.

According to an embodiment of this presentation, the term "arranging a biological sample", can mean introducing a biological sample in the transparent container (for example in an incubation chamber of the transparent container) via a pipette port, e.g., a top pipette port. According to an embodiment of this presentation, the biological sample can be arranged in the transparent container together with a reagent. The biological sample can be arranged before, after or simultaneously with arranging said reagent in said container. According to an embodiment of this presentation, the biological sample can be arranged in the transparent container as a mixture with a reagent (i.e., the biological sample is mixed with said reagent and the resulting mixture is then arranged in the transparent container.

According to an embodiment of this presentation, a "reagent" can be capable of complexing with (e.g., binding to) an analyte to be detected in the biological sample to form a reagent-analyte complex. According to an embodiment of this presentation, the reagent comprises or consists of an antibody directed against a red blood cell antigen (e.g., against a blood group antigen), red blood cells or coated particles (e.g., latex particles, microspheres or microparticles) having an antigen, antibody or any other analyte ligand thereon, or a mixture thereof.

According to an embodiment of this presentation, the biological sample can comprise or consists of blood (for example whole blood), a blood derivative (for example plasma, serum and/or red blood cells) or a mixture thereof. A test medium and in particular a fluid test medium as described herein can be any medium that comprises a separation matrix providing a sieving effect in such a way that upon the action of centrifugal forces, an analyte to be detected, when present in the biological sample, will either (i) be retained on or within the separation matrix if an analyte/reagent complex (or an analyte/reagent/reticulation agent complex) is formed or (ii) sediment beneath separation matrix in the absence of such complex.

According to an embodiment of this presentation, the separation matrix can be an inert material, i.e., a material that does not enter into any unspecific reactions with an analyte to be detected or with a reagent or a reticulation agent as defined herein. Exemplary inert materials include but are not limited to, agarose, polyacrylamide, polydextran, styrene-divinylbenzene polymers, or glass beads. According to an embodiment of this presentation, the separation matrix can be a gel, e.g., a gel comprising dextran acrylamide.

According to an embodiment of this presentation, the fluid test medium can comprise at least a separation matrix (for example a gel) and a supernatant (e.g., a liquid supernatant). According to an embodiment of this presentation, the fluid test medium can further comprise a reagent, which can be present, for example, in the separation matrix and/or in the supernatant. According to an embodiment of this presentation, the fluid test medium can further comprise a reticulation agent, which can be present, for example, in the supernatant and/or in the separation matrix. As used herein, a reticulation agent can be a biomolecule capable of crosslinking antibodies, sensitized red blood cell or sensitized particles. Exemplary reticulation agents include, but are not limited to, a secondary antibody (e.g., anti-human globulin (anti-human IgG antibody) or anti-human IgA antibody), Protein A, and streptavidin.

Figure 3:
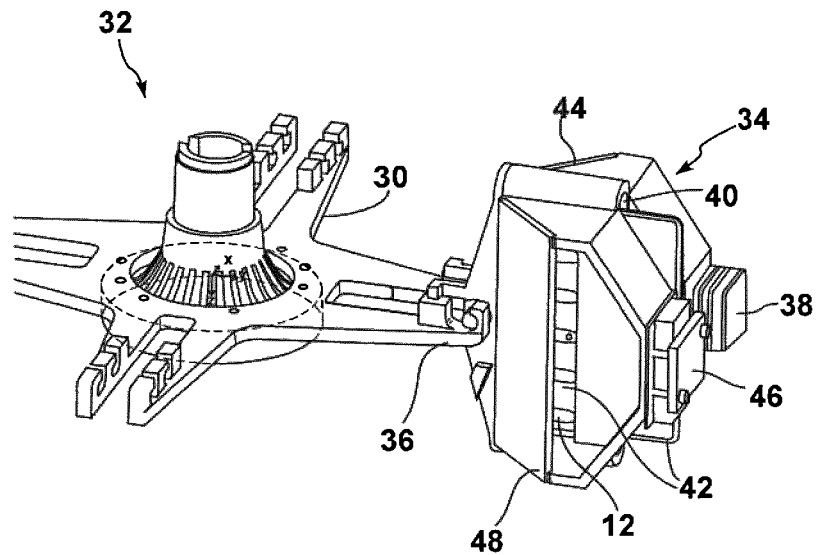
FIG. 3 is a partial projection view of a centrifuge using one centrifuge sample holder according to embodiments of this presentation.

FIG. 3 is a partial projection view of a centrifuge sample holder 34 having a camera for implementing the method above. Sample holder 34 is shown hingedly coupled to an end 36 of an arm of an exemplary four-arm rotor 30 of a centrifuge 32. The centrifuge comprises four arms in FIG. 3, but as detailed hereafter, it can comprise more than four arms. According to an embodiment of this presentation, the centrifuge sample holder 34 comprises a camera 38. The term "camera" is used in this presentation to refer to any sensor capable of generating an image of the sample. A sensor capable of capturing data that allows generating an image of the sample can be used as a "camera" according to an embodiment of this presentation. According to an embodiment of this presentation, the centrifuge sample holder 34 comprises a recess 40 for receiving at least one a transparent container 12 to be centrifuged; and the camera 38 is arranged to image at least a desired portion of the transparent container 12 received in the recess 40.

In the illustrated embodiment, the transparent container 12 is one container of a gel card 42 and the recess 40 is shaped to slidably receive the gel card 42 from a top opening. As detailed hereafter, according to an embodiment of this presentation, recess 40 can comprise a lumen through which the gel card 42 can pass; wherein a latch maintains the gel card in the recess in a position where the camera images the containers of the gel card. The latch can be opened, for example after centrifuging, to let the gel card fall through the recess to discard the gel card.

As detailed hereafter, according to an embodiment of this presentation, the transparent container 12 can contain a fluid test medium such as a gel (and eventually its supernatant) in a narrow lumen 13, and can comprise an area above the gel (and its supernatant), such as an air-filled top section 17 of the narrow lumen 13, above which a drop of liquid reagent or biological sample can be held (in a location 15 of the container that can be used as an incubation chamber), and not being in contact with the gel/fluid test medium 14, for example separated from the gel (and its supernatant)/fluid test medium by a bubble of air (also referred to as "air gap"). According to an embodiment of this disclosure, a gel card 42 can comprise: a reaction chamber, which comprises the gel 14 and its supernatant; an incubation chamber, which is able to receive the sample to be tested and which lies above the reaction chamber; and an air gap, which physically separates the two above chambers.

The centrifuging of transparent container 12 in sample holder 34 causes the biological sample (and reagent(s) that may have been added to the incubation chamber) to move toward the gel/fluid test medium, then come in contact with reagent(s) and/or reticulation agent(s) that may be present in the gel and/or its supernatant. If an analyte to be detected is present in the biological sample, it eventually forms an analyte/reagent complex (or an analyte/reagent/reticulation agent complex) which is retained on or within the gel when mixing with the gel during centrifugation. If no analyte to be detected is present in the biological sample, the biological sample, which is denser than the gel, is displaced in the gel/fluid test medium by the centrifuge acceleration toward the outer end of the transparent container 12 after mixing with the gel. According to an embodiment of this presentation, camera 38 is arranged to image the mixing of the biological sample with the fluid test medium, and its potential displacement in the fluid test medium in transparent container 12.

According to an embodiment of this presentation, the centrifuge sample holder 34 comprises a mirror 44 arranged to direct an image of the desired portion of the gel card 42 to the camera 38. As outlined above, according to an embodiment of this presentation, transparent container 12 can be one container of a gel card 42. Gel card 42 can be identical to the gel card 10 illustrated in FIG. 1, the gel card comprising a plurality of transparent containers 12 having each a pipette port 16 (not shown in FIG. 3) and joined together so as to form a row of containers having each an opening or port along an edge of a plastic card 10. As detailed hereafter, according to an embodiment of this presentation, sample holder 34 is arranged such that the pipette port 16 of each container 12 can be accessed by a pipette when the gel card 42 is received in the recess 40. In particular, when the centrifuge is not in rotation the sample holder dangles from its hinge at the end 36 of the arm of the centrifuge such that recess 40 essentially follows a vertical plane, thus maintaining the transparent container tubes 12 vertical with their pipette port 16 accessible each by a pipette located above the centrifuge.

According to an embodiment of this presentation, the camera 38 is arranged to image at least a desired portion of each of the containers 12 of gel card 42. According to an embodiment of this presentation, said desired portion of the containers 12 of gel card 42 is transparent, and camera 38 is arranged to image the biological sample in containers 12. In the example illustrated in FIG. 3, the camera 38 is arranged such that the axis of the field of vision of the camera 38 is parallel to the plane of the gel card 42, and the mirror 44 is arranged with a 45 degree angle with respect to the axis of the field of vision of the camera 38. This causes light coming from the gel card 42 to turn ninety degrees to be directed toward the camera 38; and allows arranging gel card 42 in the focal plane of camera 38 with only a limited increase of thickness of the sample holder 34 (about $1/\sqrt{2}$ times the height of mirror 44) whatever the focal length of camera 38 be. This allows for example using a single camera 38 capable of imaging at the same time all the containers 12 of gel card 42.

According to an embodiment of this presentation (shown hereafter in FIG. 6B), camera 38 can comprise two cameras 38', 38" (or more) arranged each to image different containers 12 of gel card 42. Alternatively, the two cameras can be arranged to image each different portions of same containers.

According to an embodiment of this presentation, centrifuge sample holder 34 further comprises a source of light 46; said source of light being arranged for illuminating at least said desired portion of the transparent containers 12 that is imaged by the camera. In the example illustrated, one side of all the transparent containers 12 is facing camera 38 (via the mirror 44) and the source of light 46 is arranged for directing light to an opposite side of the transparent containers 12, said light illuminating the content of the containers by transparency, so that it can be imaged by the camera. The source of light can be a LED source of light (having one or more Light Emitting Diodes). The source of light can comprise its own source of power (battery) or use power from the camera or from the centrifuge. In an alternative, the source of light could be arranged to illuminate the face of the sample that is imaged by the camera. In the example illustrated, the source of light 46 is arranged to emit light in a direction parallel to the gel card 42, and a further mirror 48 is arranged to redirect said light perpendicular to the gel card 42. This allows illuminating all of the containers 12 of gel card 42 with a single source of light 46 with only a limited increase of thickness of the sample holder 34 (about $1/\sqrt{2}$ times the height of further mirror 48), whatever distance is needed between the gel card 42 and the source of light 46 to fully illuminate all of the containers 12 with only source of light 46.

According to an embodiment of this presentation (shown hereafter in FIG. 6B), source of light 46 can comprise two sources 46', 46" (or more) arranged each to illuminate different containers 12 of gel card 42. Advantageously, a sample holder 34 according to an embodiment of this presentation is provided for being coupled to the arm of a regular centrifuge. Thus, assembling a centrifuge according to an embodiment of this presentation can comprise only replacing the known sample holders of a known centrifuge by sample holders according to an embodiment of this presentation.

Figure 4:
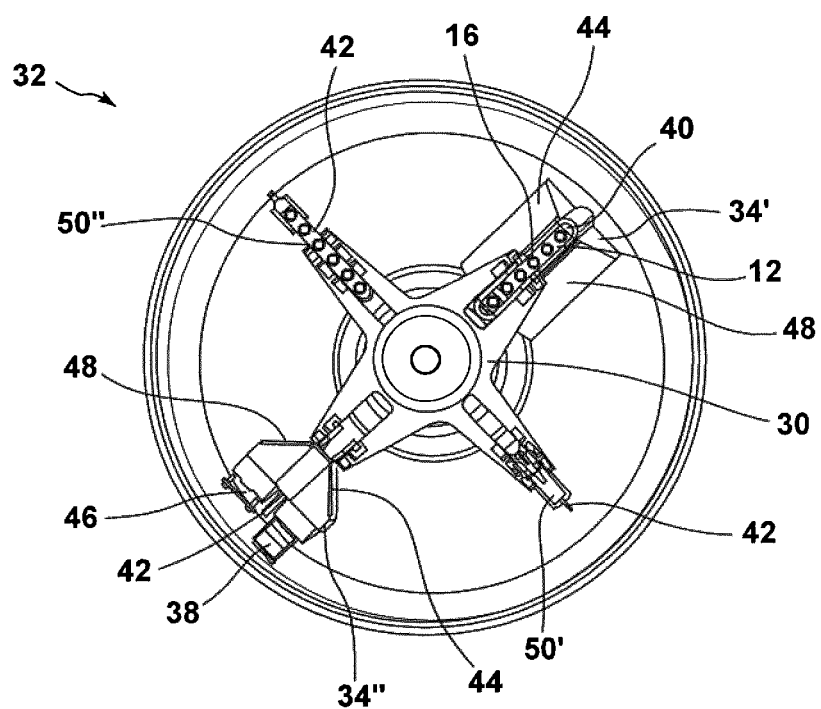
FIG. 4 is a top view of a centrifuge using two centrifuge sample holders according to embodiments of this presentation.

FIG. 4 is a top view of the centrifuge 32 of FIG. 3, carrying two centrifuge sample holders 34', 34" identical to the centrifuge sample holder 34 illustrated in FIG. 3 for implementing a method according to embodiments of this presentation. For ease of reference, centrifuge sample holder 34' is illustrated as returning back to a vertical rest position whereas sample holder 34" is illustrated in a horizontal position as taken during centrifuging. For ease of comparison, two arms of the centrifuge of FIG. 4 hingedly carry at their end known identical sample holders 50', 50" provided each for carrying a gel card 42. Sample holder 50' is illustrated in a horizontal position as taken during centrifuging, and sample holder 50" is illustrated in a vertical rest position.

Figure 5A:
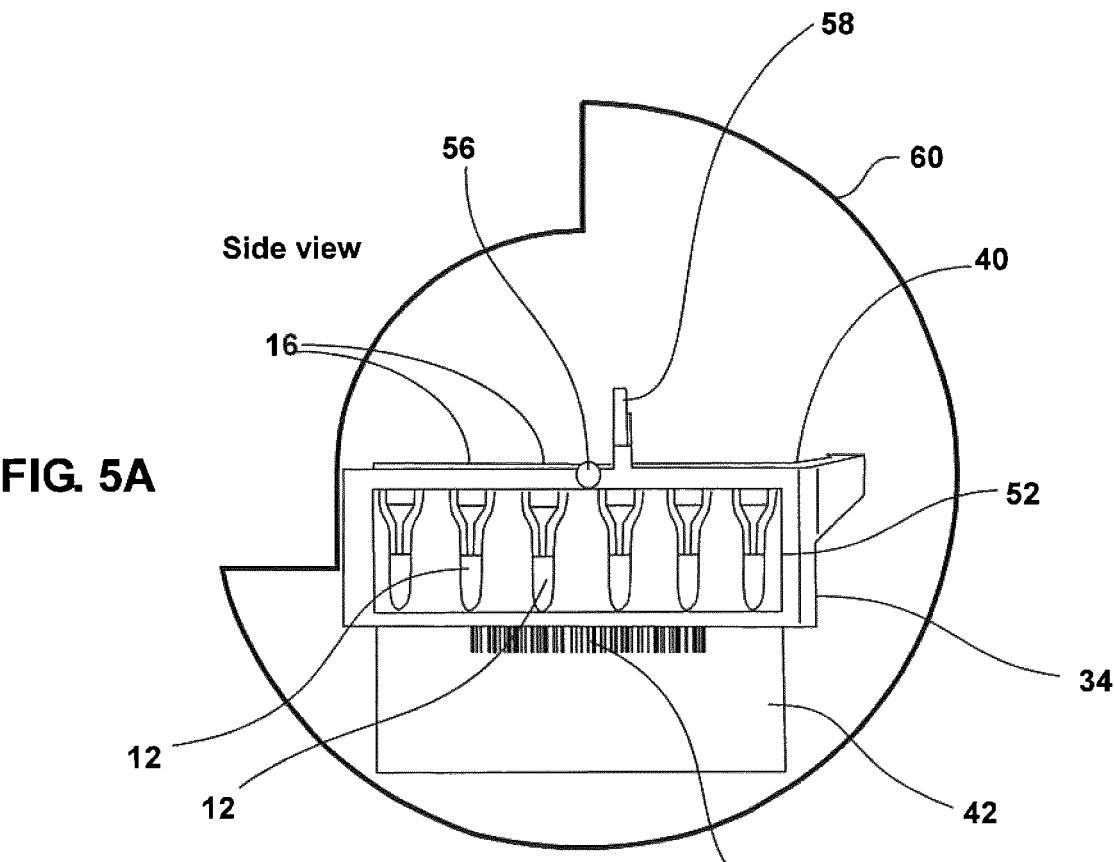
FIG. 5A is a side view of a portion of a centrifuge sample holder according to embodiments of this presentation.

FIG. 5A is a side view of a cross-section of centrifuge sample holder 34 of FIG. 3, showing sample gel card 42 held in recess 40. Gel card 42 is illustrated as having six containers 12, but embodiments of this presentation can be adapted to any appropriate sample card having any desired number of containers (or can be adapted to any appropriate transparent container). According to an embodiment of this presentation, a side opening 52 on a wall of recess 40 exposes the containers 12 of gel card 42 such that the containers (and their content) are visible from a side of centrifuge sample holder 34. According to an embodiment of this presentation, gel card 42 can bear an identification code, for example a marking 54 that can be read to track gel card 42. The marking 54 can be a bar-code. The marking 54 can be read by camera 38. As outlined above, gel card 42 can be illuminated by transparency. This can be accomplished through a side opening (not shown) symmetrical to side opening 52 with respect to gel card 42. FIG. 5A also illustrates an axis 56 allowing to hingedly connect sample holder 34 to the centrifuge, as well as a flange 58 that prevents the sample holder 34 from rotating to a position where the port openings 16 of gel card 42 would be facing even slightly downward. Finally, FIG. 5A illustrates the area of space 60 that is occupied by sample holder 34 (including elements not shown in FIG. 5A) in the plane of the cross section, between the rest and centrifuging positions of sample holder 34. Space 60 illustrates that a centrifuge comprising at least one sample holder according to this presentation must comprise a tore-shaped volume of free space corresponding to a rotation of space 60 around the axis of the centrifuge, to allow unhindered rotation of the sample holder 34. According to an embodiment of this presentation, the free space required to allow unhindered rotation of the sample holder 34 is essentially identical to the free space required to allow unhindered rotation of a known sample holder such as 50', 50" as shown in FIG. 4.

Figure 5B:
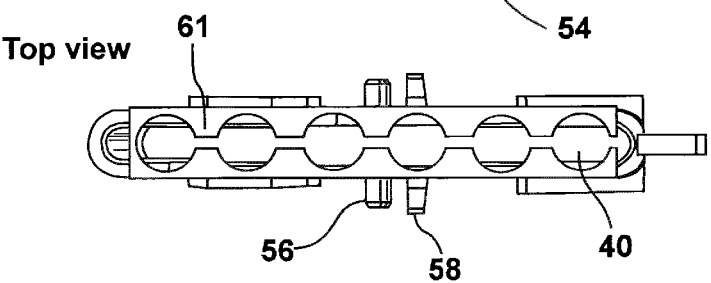
FIG. 5B is a top view of the portion of the centrifuge sample holder of FIG. 5A.

FIG. 5B is a top view of the portion of the centrifuge sample holder of FIG. 5A. According to an embodiment of this presentation, the recess 40 comprises protrusions 61 arranged to cooperate with the shape of the containers 12 of gel card 42, so as to maintain the containers 12 of gel card 42 in a predetermined position when the gel card 42 is held in recess 40.

Figure 6A:
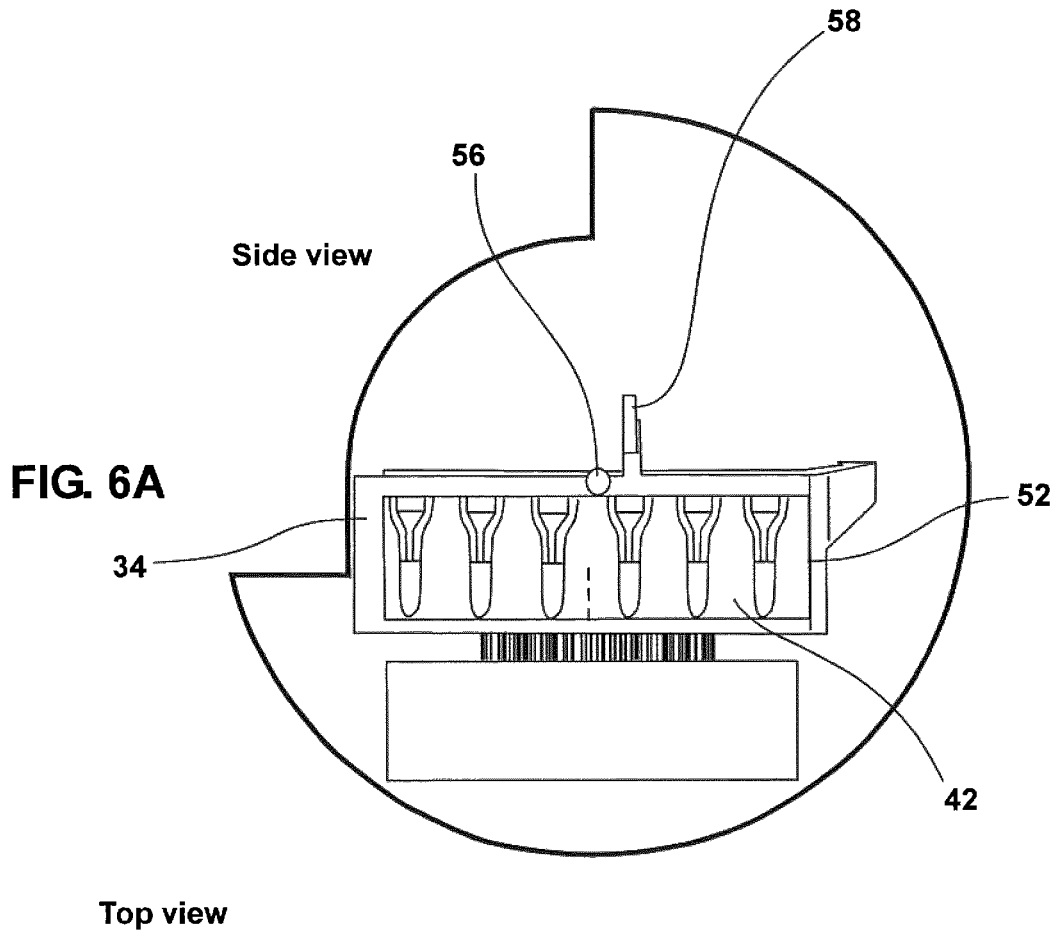
FIG. 6A is a side view of portions of a centrifuge sample holder according to embodiments of this presentation.
Figure 6B:
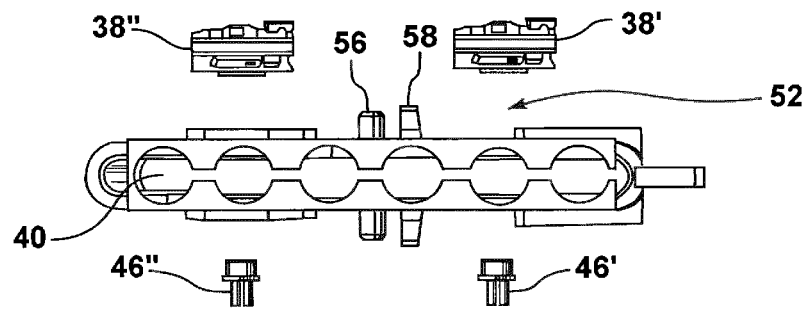
FIG. 6B is a top view of the portions of the centrifuge sample holder of FIG. 6A.
Figure 6C:
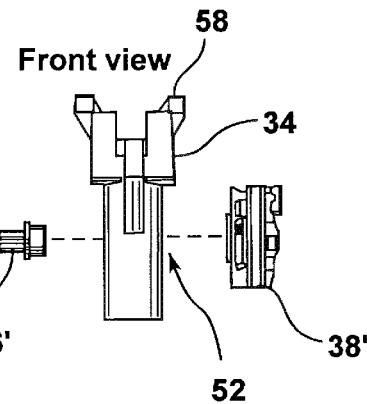
FIG. 6C is a front view of the portions of the centrifuge sample holder of FIG. 6A.

FIGS. 6A, 6B and 6C are respectively a side view, a top view, and a front view showing the position of the light source and camera of a centrifuge sample holder according to embodiments of this presentation. FIG. 6A is essentially identical to FIG. 5A above. FIG. 6B, in addition to showing the same elements as FIG. 5B, also shows how two cameras 38', 38" and two sources of light 46', 46" are arranged with respect to recess 40 in a sample holder 34 according to an embodiment of this presentation. For clarity, the mechanical structures maintaining in position the cameras and sources of light are not illustrated. According to an embodiment of this presentation, camera 38' is arranged with the axis of its field of vision directed at side opening 52, such that camera 38' can image directly a desired portion of gel card 42 when gel card 42 is held in recess 40. No mirror 44 such as described previously is used in the embodiment of FIGS. 6A-C. In the embodiment illustrated in FIG. 6B, camera 38' is arranged to image a first half of the containers of gel card 42; and a second camera 38" is arranged consistently to image the other half of the containers of gel card 42. The portion of gel card 42 that can be imaged by a camera depends of the field of vision of the camera as well as of its focal depth.

In the embodiment illustrated in FIG. 6B, the cameras 38', 38" have each a small focal depth, which allows arranging the cameras as a small distance from the recess 40, but also a narrow field of vision, whereby each camera can only image a portion of the sample and more than one camera is necessary to image properly the sample. In the embodiment illustrated, sources of lights 46', 46" are arranged opposite the cameras 38', 38" with respect to recess 40 to illuminate the gel card 42 by transparency. No mirror 48 such as described previously is used in the embodiment of FIGS. 6A-C. The portion of the gel card 42 that can be illuminated by a single source of light depends from the distance between the source of light and the recess 40. Arranging two sources of light as illustrated in FIG. 6B allows having a reduced distance between the sources of light and the recess. The number of sources of light and of cameras is not necessarily identical. Alternative embodiments of this presentation are possible, where fiber optics can be used to direct light to the sample from at least one source of light, and from the sample to at least one camera. It is noted that an embodiment of this presentation using such fiber optics arrangements allows arranging the at least one source of light and camera at a location of the sample holder that does not increase the thickness of the sample holder, whereby the thickness of the sample holders can be maintained very close to the thickness of a known sample holder. According to an embodiment of this presentation, a first camera can be arranged to image a plurality of transparent containers, and additional cameras having for example a magnifying lens can be arranged to image each a specific portion of one of the transparent containers (e.g. the bottom of the container).

FIG. 6C is a front view of the portions of the centrifuge sample holder shown in FIG. 6A and FIG. 6B.

FIGS. 7A, 7B and 7C are respectively a side view, a top view, and a front view showing the position of the light source and camera of a centrifuge sample holder according to embodiments of this presentation. For clarity, the mechanical structures maintaining in position the camera and source of light are not illustrated. FIG. 7A is essentially identical to FIG. 5A above, but it additionally shows the position of a camera 38 arranged with the axis of its field of vision parallel to the plane of the gel card 42, as for example outlined in relation with FIG. 3 above. Consistently, FIG. 7B, is identical to FIG. 5B, and additionally shows camera 38, as well as one source of light 46. As in FIG. 6B, source of light 46 is arranged with respect to recess 40 such that the axis of the field of illumination of the source of light is perpendicular to the plan of gel card 42 (when gel card 42 is held in recess 40). In the embodiment illustrated in FIG. 7B, however, an optional light diffuser 62 is arranged in output of the source of light 46, so as to illuminate gel card 42 more uniformly. It is noted that a diffuser can also be used in the embodiments outlined above, in combination with one or more sources of light.

FIG. 7C is a front view of the portions of the centrifuge sample holder shown in FIG. 7A and FIG. 7B, which additionally shows the mirror 44 used to direct the light from the gel card 42 (when gel card 42 is held in recess 40) to the camera 38. Even though a single camera 38 is illustrated in FIGS. 7A-C in combination with mirror 44, a plurality of cameras can also be used. According to an embodiment of this presentation, the camera or cameras of the sample holder 34 comprise a wireless communications circuit 64 arranged for providing wireless communications 66 between the camera and a data processing circuit 68. The data processing circuit 68 can be part of the centrifuge or it can be external to it.

Figure 8:
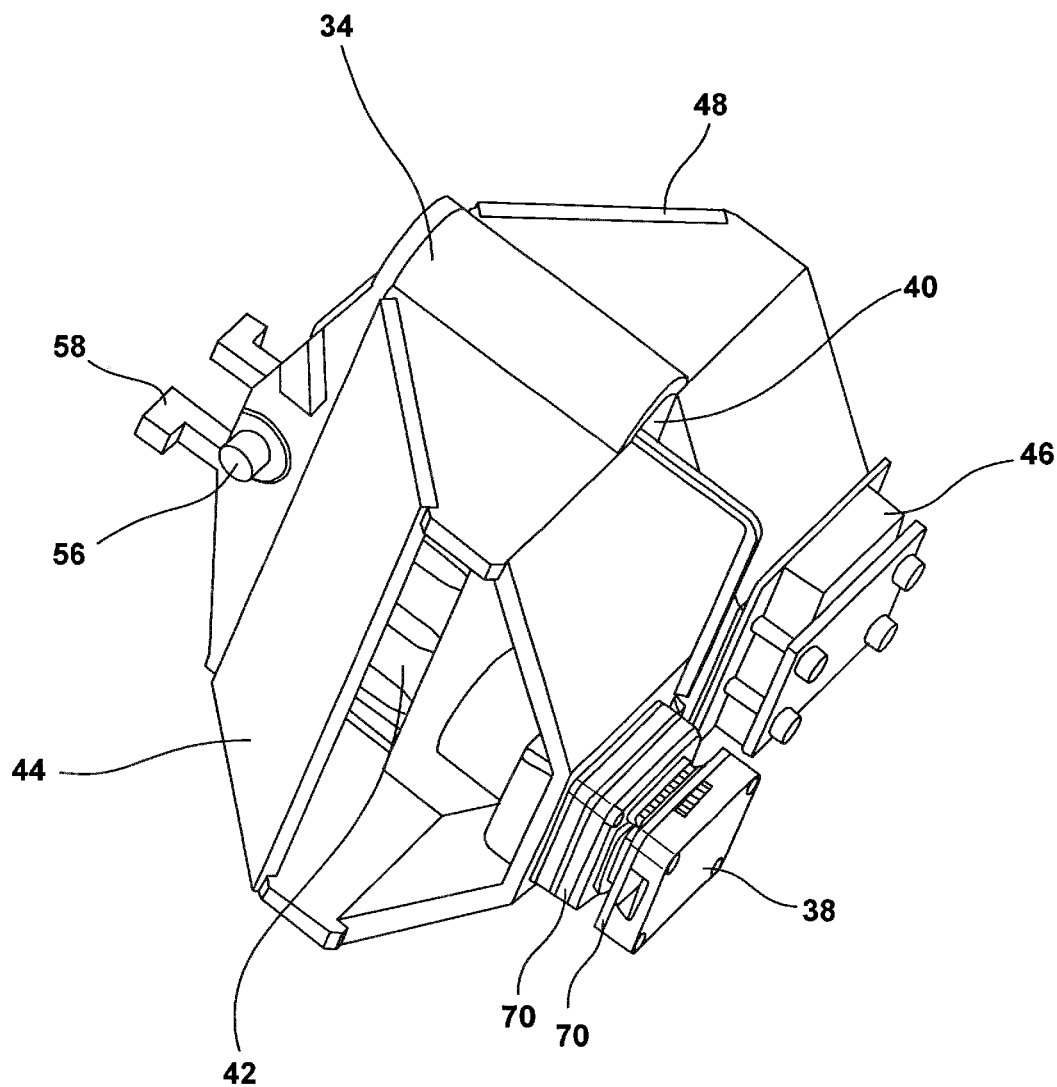
FIG. 8 is an elevation view of a centrifuge sample holder according to embodiments of this presentation.

FIG. 8 is an elevation view of a centrifuge sample holder 34 as illustrated for example in FIG. 3, oriented such that camera 38 be on the foreground of the illustration. FIG. 8 also shows the axis 56 allowing to hingedly couple the sample holder to the centrifuge and the flange 58 that prevents the sample holder 34 from rotating to a position where the port openings 16 of gel card 42 would be facing downward. As schematically illustrated in FIG. 8, camera 38 can comprise a plurality of circuit boards 70, which can comprise the communications circuit 64, data storage circuits, image processing circuits and/or a power source (e.g. battery) for the camera. As in FIG. 3 before, FIG. 8 shows gel card 42 held in recess 40. According to an embodiment of this presentation, circuit boards 70 can comprise an accelerometer and/or a goniometer circuit arranged for issuing data that can be correlated with the images captured by the camera.

Figure 9:
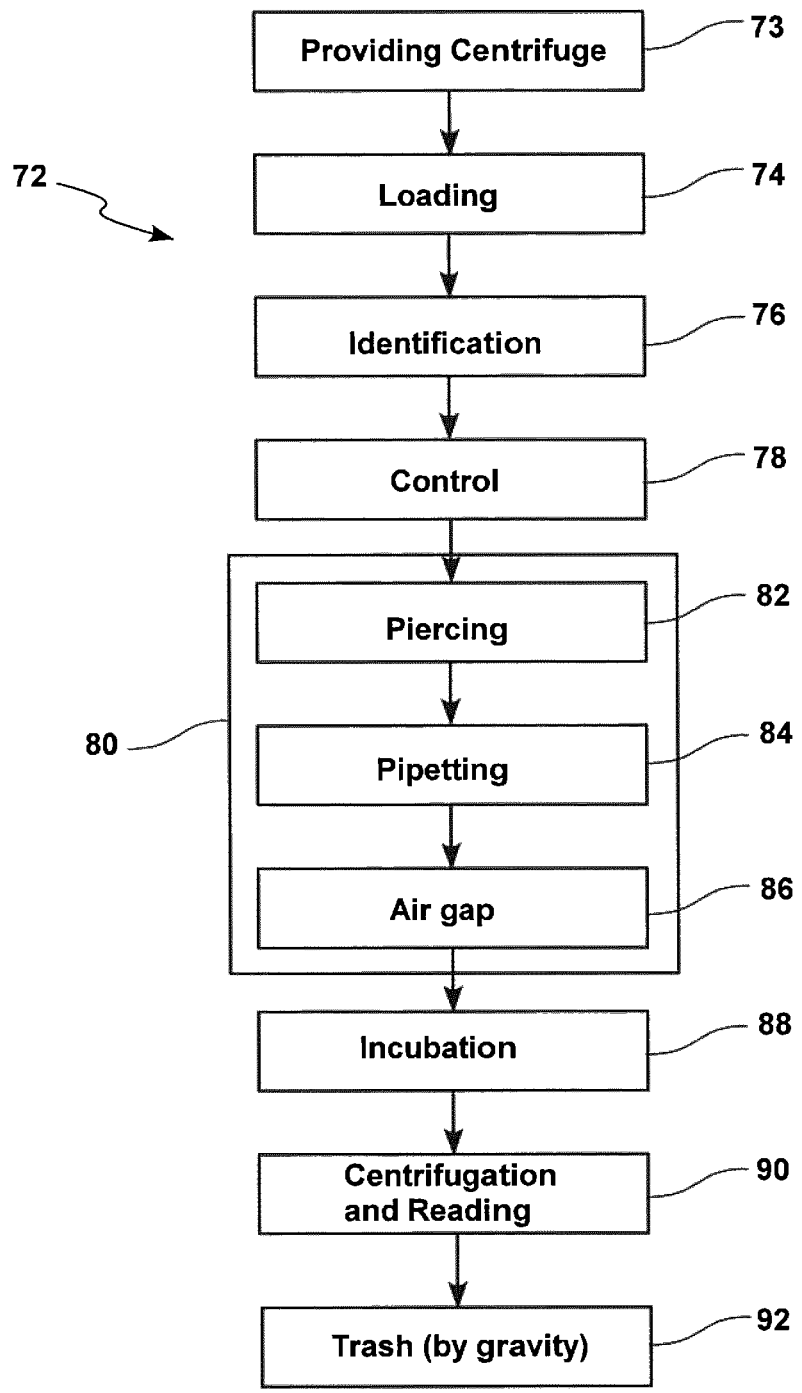
FIG. 9 illustrates a method according to embodiments of this presentation.

FIG. 9 illustrates a method 72 of using a centrifuge having a sample holder according to embodiments of this presentation, the method comprising: providing 73 a centrifuge sample holder having a camera; and arranging a transparent container comprising a test medium in a recess of said centrifuge sample holder, wherein the camera is arranged to image a portion of the container comprising said test medium (loading 74). The method further comprises arranging said biological sample above and not in contact with said test medium in said container (pipetting 84, eventually after piercing 82); and with the camera, imaging a mixing of said biological sample with said test medium while centrifuging the sample holder (centrifuging and reading 90).

In an embodiment as illustrated in FIG. 3, the "loading" of the container can involve dropping a gel card 42 with transparent container 12 into the recess 40 of sample holder 34. The method can then comprise identifying 76 the sample in at least container 12. In an embodiment as illustrated in FIG. 3, this can involve reading with the camera 38 an identification code 54 on gel card 42, for example when the gel card 42 is introduced in recess 40. Alternatively, the identification code 54 can be arranged at a location on card 54 that is always visible when card 42 is maintained in recess 40. This identification step can be used to verify that the gel card 42 uses proper gel/fluid test medium. The method can then comprise controlling 78 the container 12. In an embodiment as illustrated in FIG. 3, this can involve controlling visually with the camera 38 that a gel/fluid test medium in the containers 12 of gel card 42 is intact (integrity check of the gel/fluid test medium, making sure that the gel/fluid test medium does not appear dry or mis-positioned).

The method can then comprise introducing 80 a biological sample (and, optionally, a reagent), into the container 12. In detail, this introducing of the biological sample can comprise piercing 82 a membrane (not shown) that seals the input ports 16 of the container 12 of gel card 42; then introducing 84 with a pipette a biological sample in a container 12 (for example in the incubation chamber of said container); the biological sample being for example isolated from the gel (and its supernatant)/test medium by an air bubble (or "air gap") in container 12. The method can then comprise visually checking 86 that the biological sample in the incubation chamber is actually isolated from the gel/test medium by said air bubble in container 12. The above steps ensure that the sample is prepared adequately, and are generally conducted by an operator, with or without machine assistance, when using a known centrifuge. It is noted that if for whatever reason the biological sample in a container of a gel card contacts the gel/test medium before the start of the centrifuging, for example if a prepared gel card is bumped against a hard surface when placing it in a centrifuge, the results of the centrifuging can be impaired. Thus, when using a known centrifuge extreme care is generally required at the time of loading prepared gel cards. As outlined above, a method according to an embodiment of this presentation comprises imaging with the camera the arranging a biological sample above and not in contact with the test medium (i.e., imaging the arranging of the biological sample in the incubation chamber) in each container, which allows checking automatically that the biological sample and test medium are properly positioned until the very start of the centrifuging, thus improving the reliability of the centrifuging.

Another problem of known methods of centrifuging gel cards is that the gel/fluid test medium of the gel cards can have been displaced or have dried during the storage of the card, rendering the card un-usable. Using known centrifuges thus involves visually checking the state (integrity) of the gel/fluid test medium in the containers of a gel card prior to positioning the biological sample above but not in contact with the gel/fluid test medium. As outlined above, a method according to an embodiment of this presentation comprises imaging with the camera the gel/fluid test medium in the container before arranging the biological sample above and not in contact with the gel/fluid test medium in the container. This allows checking automatically the integrity of the gel/fluid test medium in the containers prior to centrifuging, thus improving the reliability of the centrifuging.

In other words, the camera of a sample holder according to an embodiment of this presentation advantageously allows conducting automatically part or all of the identification and verification steps above. The loading of the sample card, piercing and pipetting steps can also be conducted automatically. Thus, a sample holder according to embodiments of this presentation physically allows the automatization of all the manual steps that are necessary for preparing a sample for centrifuging in a known centrifuge. Such automation represents large gains in cost and reliability of centrifuging.

According to an embodiment of this presentation the sample prepared in steps 74-80 can then be incubated 88 if required, before centrifuging 90. According to an embodiment of this presentation, sample holder 34 can comprise an incubator module allowing for example to maintain gel card 42 to a predetermined temperature for a predetermined time. The camera of the sample holder 34 according to an embodiment of this presentation advantageously allows observing the sample throughout the centrifuging. The output of the camera can be recorded and/or transmitted for analysis. A data processor circuit board 70 can pre-process the data recorded or transmitted, if appropriate. Thus, a sample holder according to embodiments of this presentation also physically allows the automatization of the observation of the results of the centrifuging, in addition to permitting to observe how the sample changes during centrifuging.

Advantageously, the centrifuging can be stopped if the real-time observation of the centrifuged biological samples in all the sample holders of a centrifuge according to an embodiment of this presentation show a completed reaction, thus allowing an optimization of the use of the centrifuge. Advantageously, observing how a biological sample changes during centrifuging can in certain case allow determining rapidly the result of the centrifuging. For example, when reacting blood or a blood derivative from a patient with various reagents to determine what blood or blood derivative can be transfused to said patient, some sampled bloods or blood derivatives react very rapidly and such reaction can be observed immediately using embodiments of this presentation. Also, for reactions that are not as fast, a neural network can be trained to recognize a centrifuging outcome based on the images of the first minutes or seconds of a centrifuging. A gain of one or more minutes can be a life-saving gain when dealing with testing what blood or blood derivative can be transfused to a patient. With embodiments of this presentation, the result of the centrifuging (e.g. sample blood or a blood derivative compatible with a determined transfusion blood) can advantageously be known rapidly without any need to stop the centrifuging (other samples can still be centrifuged and have not yielded results yet). Thus, embodiments of this presentation allow centrifuging a plurality of samples and at the same time obtaining centrifuging results very rapidly, which represents a significant advantage with respect to currently used centrifuges where all the samples are centrifuged for a fixed time before being downloaded to a sample-reading machine.

Optionally, a sample holder 34 can provide a latch that allows to automatically trash 92 the gel card after centrifuging; for example by controllably letting card 42 fall through recess 40 to a waste location.

An embodiment of this presentation provides for imaging with the camera the top surface of the fluid test medium, so as to image the supernatant while centrifuging the sample holder.

Figure 2:
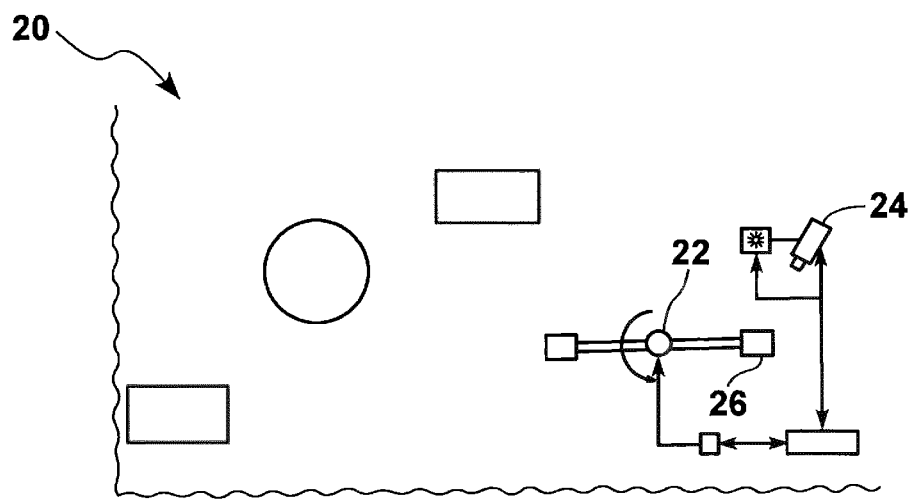
FIG. 2 illustrates a known centrifuge with imaging capability.
Figure 10:
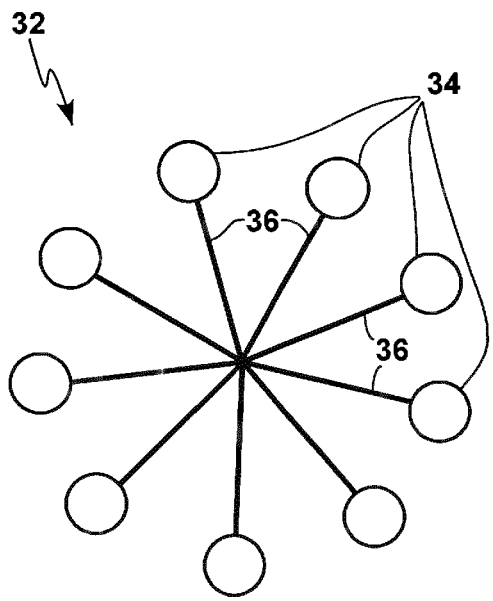
FIG. 10 illustrates schematically a centrifuge according to an embodiment of this presentation.

FIG. 10 illustrates very schematically a centrifuge 32 according to an embodiment of this presentation, comprising a rotor with a plurality of arms having each an outer end 36 coupled to a respective centrifuge sample holder 34 according to an embodiment of this presentation, wherein the outer end 36 of each arm is hingedly coupled to its respective sample holder 34, as for example illustrated in FIG. 3. According to an embodiment of this presentation, the centrifuge 32 comprises more than four arms. As detailed above, a sample holder according to an embodiment of this presentation can have a thickness that is only slightly superior to the thickness of a known sample holder. Thus, a centrifuge 32 as illustrated in FIG. 10 can have a number of arms similar to the number of arms found in a known centrifuge. Further, because each sample holder according to an embodiment of this presentation comprises at least a camera, increasing the number of arms of the centrifuge does not impair the ability to capture images of the sample and does not condition the performance of the cameras, contrary to the contraption illustrated in FIG. 2.

Figure 11:
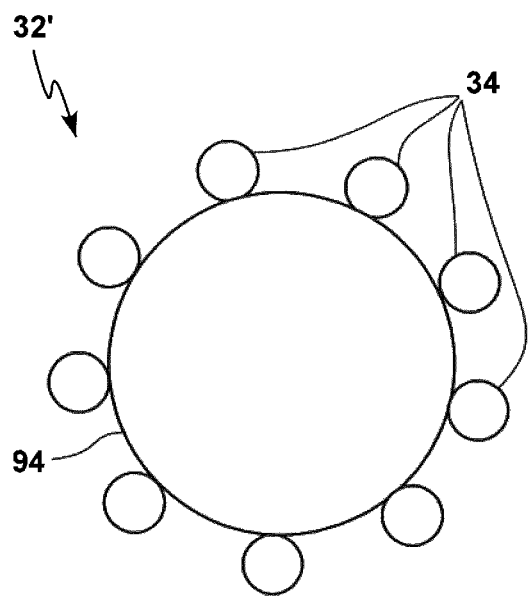
FIG. 11 illustrates schematically a centrifuge according to an embodiment of this presentation.

FIG. 11 illustrates schematically a centrifuge 32' similar to the centrifuge 32 illustrated in FIG. 10, with the difference that centrifuge 32' comprises a circular rotor 94 having an outer periphery in lieu of the multiple arms of centrifuge 32. A plurality (for example more than 4) of sample holders according to an embodiment of this presentation are hingedly coupled to the rotor along said outer periphery.

Figure 12:
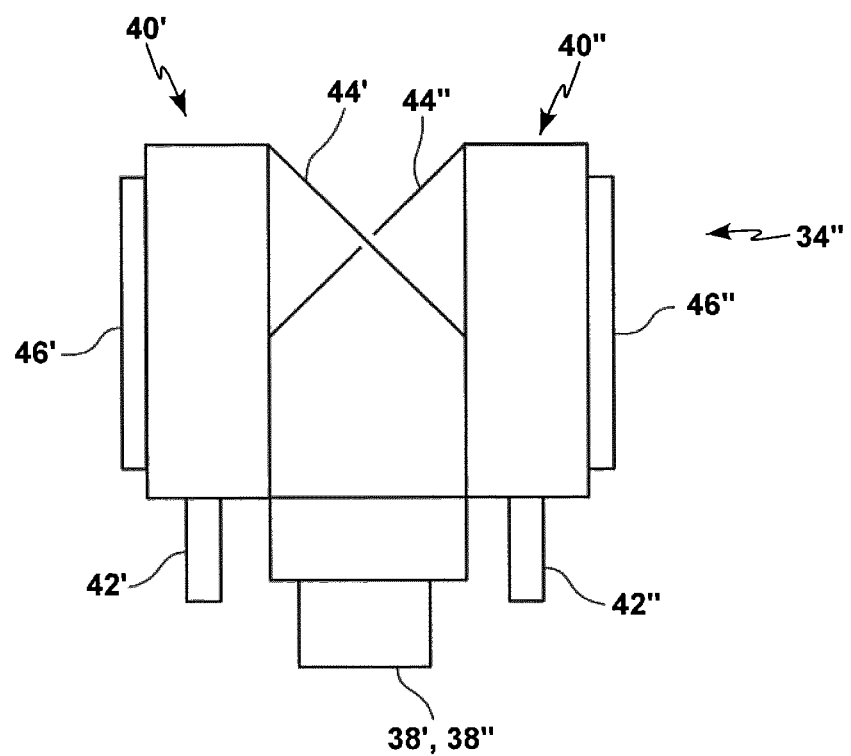
FIG. 12 is a side view of a centrifuge sample holder according to an embodiment of this presentation.

FIG. 12 is a side view of a centrifuge sample holder 34''' according to an embodiment of this presentation, that is provided for receiving two gel cards 42', 42'', each in a distinct recess 40', 40''; comprising two cameras 38', 38'' and two mirrors 44', 44'' arranged in tandem and angled each for allowing cameras 38', 38'' to respectively image the containers of the gel cards 42', 42''. Sample holder 34''' can also comprise two sources of light 46', 46'', for example such as smartphone backlight sources, arranged each for illuminating the containers of the gel cards 42', 42'' by transparency.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. For example, in the description above the samples are mainly described as gel cards. However, embodiments of this presentation can as well be arranged to receive test tube samples (biological samples in one or more test tubes) or bottle samples (biological samples in one or more test bottles) or microplate samples (biological samples analyzed in one or more cavity of a microplate).

No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this presentation with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this presentation is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

All elements, parts and steps described herein are preferably included. It is to be understood that any of these elements, parts and steps may be replaced by other elements, parts and steps or deleted altogether as will be obvious to those skilled in the art.

Broadly, this writing discloses at least the following: a method of testing a biological sample, the method comprising: providing a centrifuge sample holder having a camera; arranging a transparent container comprising a fluid test medium in a recess of said centrifuge sample holder, wherein the camera is arranged to image a portion of the container comprising said fluid test medium; arranging said biological sample above and not in contact with said fluid test medium in said container; and with the camera, imaging a mixing of said biological sample with said fluid test medium while centrifuging the sample holder.

What is claimed is:

1. A method of testing a biological sample, the method comprising:
   providing a centrifuge comprising a rotor comprising one or more arms;
   providing a centrifuge sample holder comprising an axis for hingedly coupling the centrifuge sample holder to an arm of the one or more arms of the rotor, a recess extending in a vertical direction when the centrifuge is not rotating, and a camera directly attached to an external surface of a wall of the centrifuge sample holder surrounding the recess;
   arranging a transparent container comprising a test medium in the recess of said centrifuge sample holder such that the container has a fixed relationship with the camera directly attached to the centrifuge sample holder, wherein the camera is arranged at a location on the external surface of the centrifuge sample holder to image a portion of the container comprising said test medium;

arranging said biological sample in a location of said container above and not in contact with said test medium in said container in vertical orientation when the centrifuge is not rotating; and with the camera, imaging a mixing of said biological sample with said test medium while centrifuging the sample holder.

2. The method of claim 1, further comprising imaging with the camera said biological sample in said location of said container above and not in contact with said test medium in said container.

3. The method of claim 1, further comprising imaging with the camera said test medium in said container before said arranging of said biological sample in said location of said container above and not in contact with said test medium in said container.

4. The method of claim 1, further comprising imaging with the camera a top surface of the test medium while centrifuging the sample holder.

5. The method of claim 1, further comprising providing a mirror between the camera and the container.

6. The method of claim 1, wherein the recess is arranged for receiving a plurality of transparent containers comprising each a test medium, wherein the camera is arranged to image at least a portion of each of said plurality of containers received in said recess.

7. The method of claim 6, wherein the plurality of transparent containers are joined together so as to form a row along an edge of a plastic card.

8. A biological sample centrifugation apparatus, the apparatus comprising:

a rotor having one or more arms; and a centrifuge sample holder having a camera directly attached to an external surface of a wall of the centrifuge sample holder surrounding a recess;

the centrifuge sample holder comprising an axis for hingedly coupling the centrifuge sample holder to an arm of the one or more arms of the rotor, the recess extending in a vertical direction when the centrifuge is not rotating and arranged for receiving a transparent container comprising a test medium, such that the container has a fixed relationship with the camera attached to the centrifuge sample holder, wherein the camera is arranged at a location on the external surface on the centrifuge sample holder to image a portion of the container comprising said test medium when said container is received in said recess;

the camera being arranged for, while the container is centrifuged, imaging a mixing of said test medium with a biological sample, wherein the biological sample is arranged prior to centrifuging the container, in a location of said container above and not in contact with said test medium in said container.

9. The apparatus of claim 8, wherein the camera is arranged on an external surface of the sample holder and configured for imaging said biological sample being arranged in said location of said container above and not in contact with said test medium in said container.

10. The apparatus of claim 8, wherein the camera is arranged on an external surface of the sample holder and configured for imaging said test medium in said container before said biological sample being arranged in said location of said container above and not in contact with said test medium in said container.

11. The apparatus of claim 8, wherein the camera is arranged for also imaging a top surface of the test medium while centrifuging the sample holder.

12. The apparatus of claim 8, comprising a mirror between the camera and the container.

13. The apparatus of claim 8, comprising a source of light arranged for illuminating the portion of the container comprising said test medium that is imaged by the camera.

14. The apparatus of claim 8, wherein the recess is arranged for receiving a plurality of transparent containers comprising each a test medium, wherein the camera is arranged to image at least a portion of each of said plurality of containers received in said recess.

15. The apparatus of claim 14, wherein the plurality of transparent containers are joined together so as to form a row along an edge of a plastic card.

16. The apparatus of claim 8, wherein the transparent container is a gel card, and wherein the camera is positioned on the centrifuge sample holder such that an axis of field of vision of the camera is parallel to a plane of the gel card.

* * * * *